United States Patent
St. Pierre et al.

(10) Patent No.: US 10,098,553 B2
(45) Date of Patent: Oct. 16, 2018

(54) BLOOD PRESSURE MONITORING SYSTEM AND METHOD

(75) Inventors: Shawn C. St. Pierre, Syracuse, NY (US); Sean R. Karla, Syracuse, NY (US); Lari E. Rutherford, Jamesville, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 865 days.

(21) Appl. No.: 13/606,967

(22) Filed: Sep. 7, 2012

(65) Prior Publication Data

US 2013/0245467 A1  Sep. 19, 2013

Related U.S. Application Data

(60) Provisional application No. 61/532,719, filed on Sep. 9, 2011.

(51) Int. Cl.
*A61B 5/022* (2006.01)
*A61B 5/00* (2006.01)

(52) U.S. Cl.
CPC ........ *A61B 5/02225* (2013.01); *A61B 5/7246* (2013.01); *A61B 5/0002* (2013.01); *A61B 2560/0223* (2013.01)

(58) Field of Classification Search
None
See application file for complete search history.

(56) References Cited

U.S. PATENT DOCUMENTS

| | | | |
|---|---|---|---|
| 5,289,823 A | 3/1994 | Eckerle | |
| 7,004,907 B2* | 2/2006 | Banet et al. | 600/485 |
| 2002/0082508 A1* | 6/2002 | Ogura | A61B 5/02125 600/490 |
| 2002/0147401 A1* | 10/2002 | Oka | A61B 5/02116 600/490 |
| 2006/0084878 A1* | 4/2006 | Banet et al. | 600/485 |
| 2006/0293601 A1 | 12/2006 | Lane et al. | |

(Continued)

FOREIGN PATENT DOCUMENTS

WO    2005020808 A1    3/2005

OTHER PUBLICATIONS

Hahn, Lorraine P., et al. "Prevalence and accuracy of home sphygmomanometers in an urban population." American journal of public health 77.11 (1987): 1459-1461.*

(Continued)

*Primary Examiner* — Jacqueline Cheng
*Assistant Examiner* — Jairo Portillo
(74) *Attorney, Agent, or Firm* — Merchant & Gould P.C.

(57) ABSTRACT

Systems and methods for correlating diagnostic readings obtained by at least two medical devices can include a pressure offset correction parameter that is calculated for the purpose of correlating oscillometric blood pressure readings between a "home" blood pressure monitor and an "office" blood pressure monitor. The offset correction parameter is used to adjust blood pressure readings of the "home" or "office" blood pressure monitor such that these readings can be validly compared with blood pressure readings obtained using the other blood pressure monitor. In this manner, a more complete and reliable blood pressure trend may be developed and used for managing blood pressure related medical conditions.

10 Claims, 8 Drawing Sheets

(56) References Cited

U.S. PATENT DOCUMENTS

| | | |
|---|---|---|
| 2010/0125212 A1 | 5/2010 | Kim et al. |
| 2010/0249544 A1 | 9/2010 | Sethi et al. |
| 2010/0280395 A1 | 11/2010 | Lin |
| 2010/0298721 A1* | 11/2010 | Kim ................ A61B 5/022 600/486 |
| 2011/0152697 A1* | 6/2011 | Kawamura ........ A61B 5/02152 600/485 |

OTHER PUBLICATIONS

Rotch, Allison L., et al. "Blood pressure monitoring with home monitors versus mercury sphygmomanometer." Annals of Pharmacotherapy 35.7-8 (2001): 817-822.*
"Automatic Blood Pressure Monitor with Intellisense" Omron Instruction Manual (2001).*
International Search Report and Written Opinion in PCT/US2012/054177 dated Mar. 4, 2013, 9 pages.

* cited by examiner

BLOOD PRESSURE MONITORING SYSTEM AND METHOD

RELATED APPLICATION

This application claims the benefit of U.S. Patent Application Ser. No. 61/532,719 filed on Sep. 9, 2011, the entirety of which is hereby incorporated by reference.

BACKGROUND

Automated blood pressure machines provide an easy and convenient way for healthcare professionals to obtain an in-office patient blood pressure reading. The ease of use of these machines also makes them ideal for use in a home, where patients can monitor their own blood pressure free of the stress of a medical setting.

SUMMARY

In one aspect, a method for correlating diagnostic measurements obtained by at least two different medical devices is disclosed. The method includes: obtaining a first diagnostic measurement by a first medical device; obtaining a second diagnostic measurement by a second medical device; generating a correction parameter by comparing the first and second diagnostic measurements; and adjusting one of the first diagnostic measurement and the second diagnostic measurement using the correction parameter to correlate the second diagnostic measurement to the first diagnostic measurement.

In another aspect, a method for correlating blood pressure values obtained by a first blood pressure device and a second blood pressure device is disclosed. The method includes: calculating a first blood pressure value with the first blood pressure device; calculating a second blood pressure value with the second blood pressure device; comparing the first and second blood pressure values and generating a correction value representing a difference between the first and second blood values; and modifying the second blood pressure value using the correction value to correlate the first and second blood pressure values.

In yet another aspect, a computer-implemented method for correlating blood pressure values obtained by two blood pressure devices is disclosed. The method includes: calculating a first blood pressure value from a set of oscillometric blood pressure data obtained by an office blood pressure device, the office blood pressure device being configured for use in a doctor's office; calculating a second blood pressure value with a home blood pressure device from the set of oscillometric blood pressure data obtained by the office blood pressure device, the home blood pressure device being configured for use in a patient's personal home; comparing the first and second blood pressure values; generating a correction value representing a difference between the first and second blood values; modifying the second blood pressure value using the correction value to correlate the first and second blood pressure values; transferring at least the first blood pressure value and the modified second blood pressure value to a web portal from the home blood pressure device; and generating a blood pressure trend plot including at least the first blood pressure value the modified second blood pressure value.

This Summary is provided to introduce a selection of concepts, in a simplified form, that are further described below in the Detailed Description. This Summary is not intended to be used in any way to limit the scope of the claimed subject matter. Rather, the claimed subject matter is defined by the language set forth in the Claims of the present disclosure.

DETAILED DESCRIPTION

The present disclosure is directed to systems and methods for correlating diagnostic readings between at least two medical devices. In general, differences between the two medical devices may lead to differences between measurements reported by each respective medical device.

In one example embodiment, each medical device is used to measure blood pressure. A pressure offset correction parameter is calculated for the purpose of correlating oscillometric blood pressure readings between a "home" blood pressure monitor and an "office" blood pressure monitor. The offset correction parameter is used to adjust blood pressure readings of the "home" or "office" blood pressure monitor such that these readings can be easily compared with blood pressure readings obtained by the other blood pressure monitor. In this manner, a more complete and reliable blood pressure trend may be developed and used for managing blood pressure-related medical conditions.

Although not so limited, an appreciation of the various aspects of the present disclosure will be gained through a discussion of the examples provided below.

Figure 1:
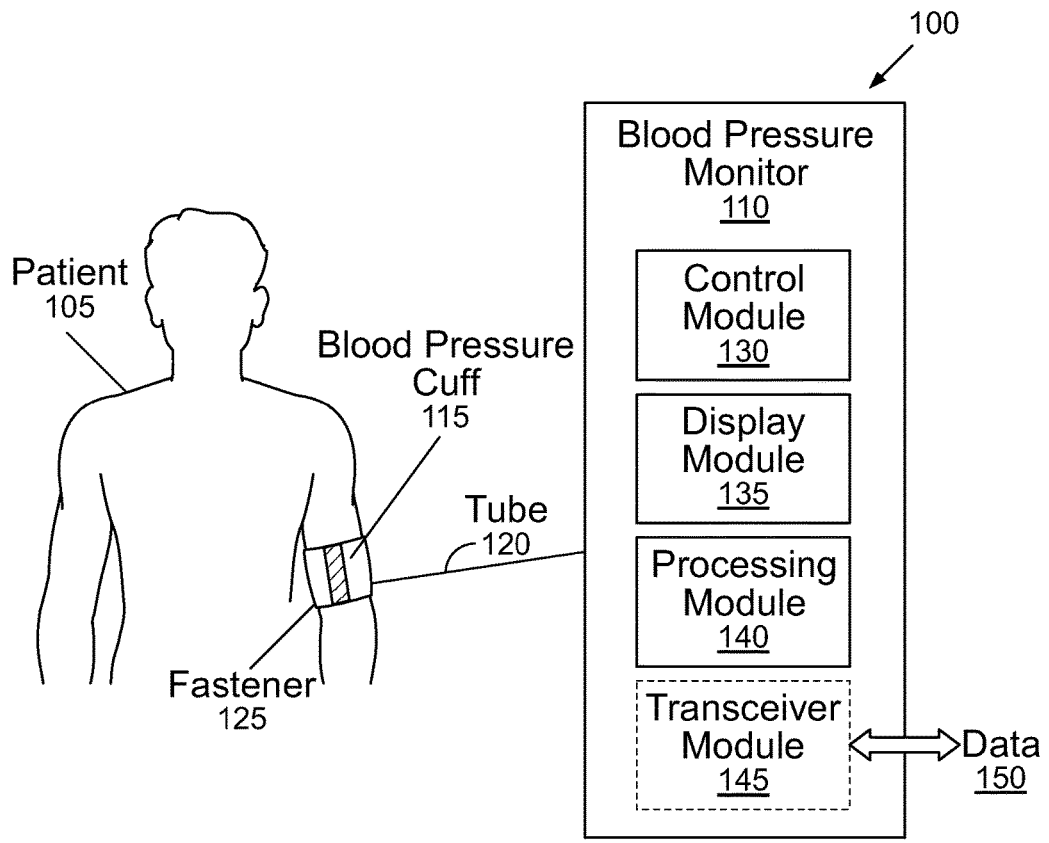
FIG. 1 shows an example environment for obtaining a blood pressure measurement.

FIG. 1 shows an example environment 100 in which an oscillometric blood pressure measurement is performed and/or obtained. The environment 100 includes a patient 105, a monitor 110, and a cuff 115. The environment 100 also includes a tube 120 that couples the cuff 115 to the monitor 110. In the example shown, the cuff 115 is positioned to the upper left arm of the patient 105, secured in place by a fastener 125 (e.g., Velcro). Other embodiments are possible.

The example monitor 110 includes a control module 130, a display module 135, and a processing module 140, each generally configured to facilitate and/or implement the blood pressure measurement. For example, the control module 130 is generally configured to perform the measurement upon user selection of a corresponding control mechanism (e.g., start selection, stop selection, etc.), while the display module 135 is configured to render a blood pressure reading (e.g., systolic/diastolic) upon completion of the measurement.

Figure 2:
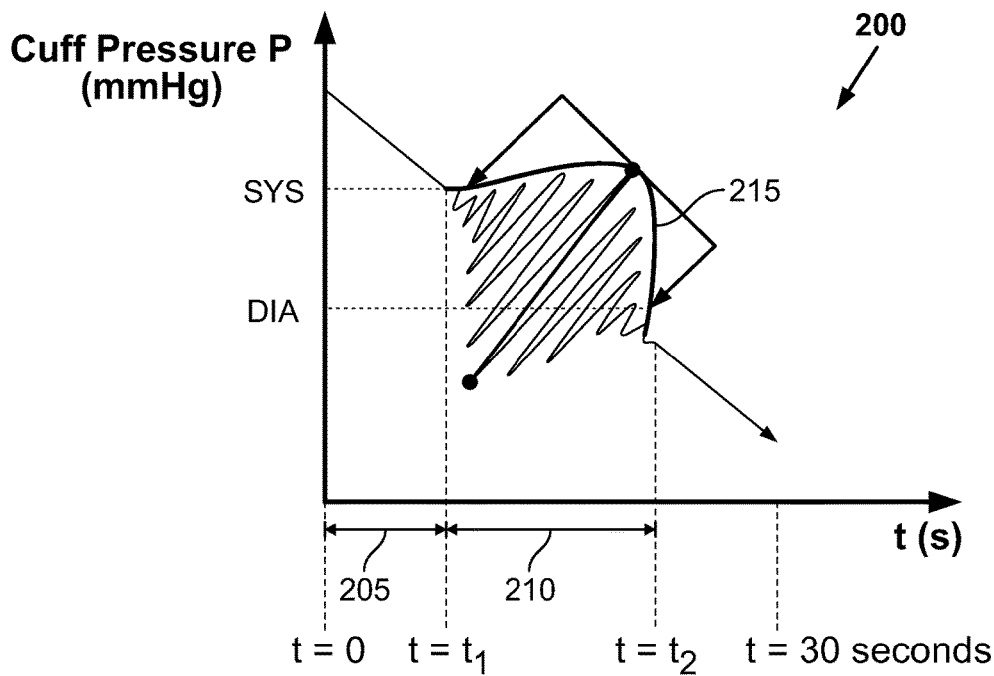
FIG. 2 shows an example pressure curve illustrating pressure recorded within a blood pressure cuff during a blood pressure measurement.

The processing module 140 is configured to control, monitor, and record pressure within the cuff 115 during the blood pressure measurement. Referring now to FIG. 2, an example pressure curve 200 is shown illustrating a pressure P recorded within the cuff 115 over an example measurement time period t=30 seconds.

In operation, the processing module 140 initially inflates the cuff 115 via the tube 120 such that at least the brachial artery within the upper left arm of the patient 105 is fully occluded. The processing module 140 then gradually reduces the pressure P within the cuff 115 during a first phase 205, defined between t=0 and t=$t_1$.

Once blood flow is present within the brachial artery, but restricted (i.e., beginning at t=$t_1$), the pressure P within the cuff 115 varies in synchrony with expansion and contraction of the brachial artery during a second phase 210, defined between t=$t_1$ and t=$t_2$. The processing module 140 continues to reduce the pressure P within the cuff 115 during the second phase 210 through the end of the measurement at t=30 seconds. The processing module 140 subsequently calculates values for the systolic pressure "SYS" and the diastolic pressure "DIA" from recorded oscillometric raw data, typically represented by an envelope 215, using a pre-defined statistical algorithm.

Other embodiments of the monitor 110 are possible. For example, in some embodiments the monitor 110 includes a transceiver module 145 (see FIG. 1) generally configured to transmit (e.g., via wireless and/or hardwire connection) information or data 150 between the monitor 110 and one or more other compatibly configured devices (e.g., other blood pressure monitors, personal computer, etc). Examples of data 150 include blood pressure reading(s), calibration parameter(s), instructions and/or comments for rendering by the display module 135, and other information, such as described in further detail below in connection with FIGS. 3-13.

Figure 3:
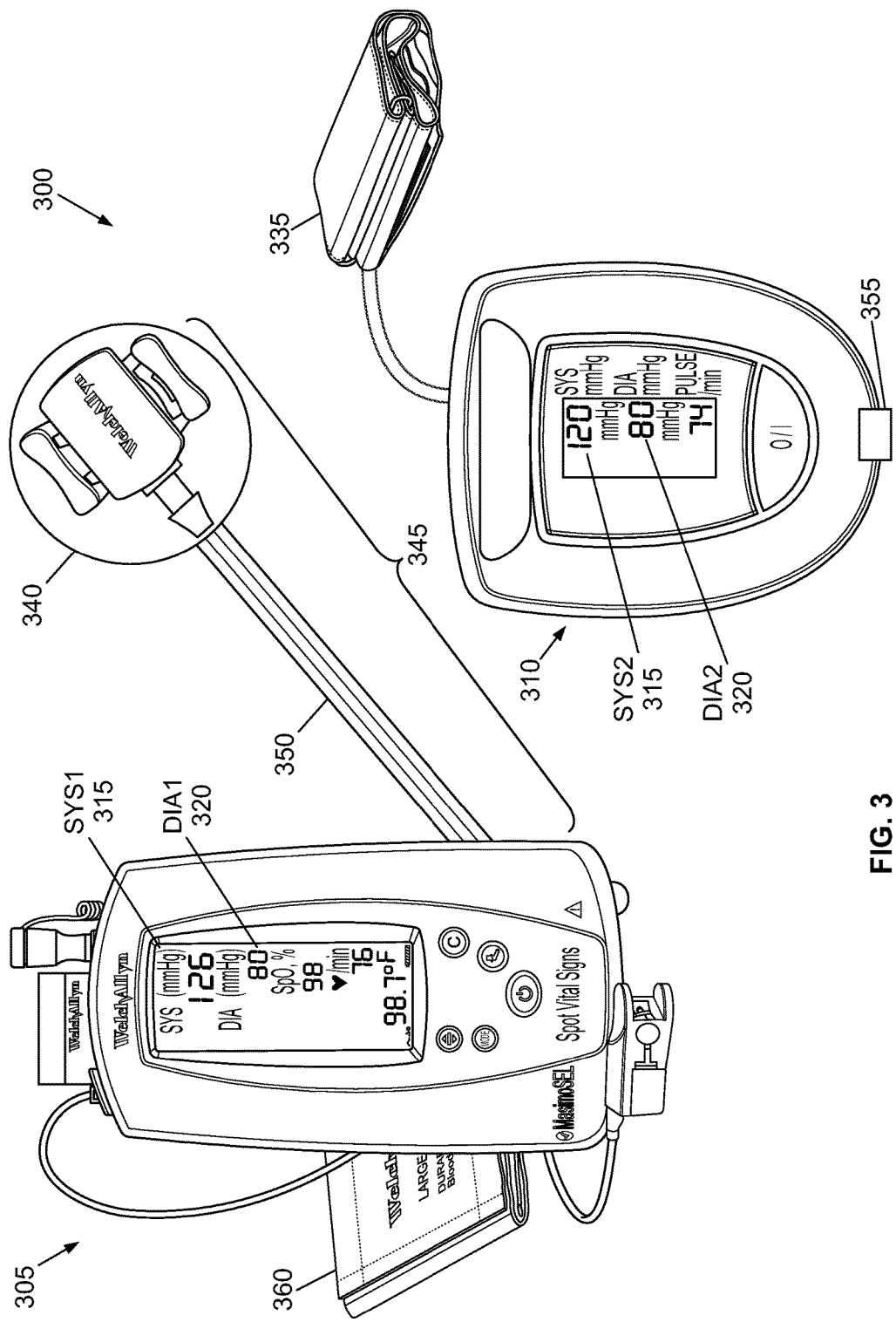
FIG. 3 shows a first example system for correlating blood pressure readings between first and second blood pressure monitors.

Referring now to FIG. 3, a first example system 300 for correlating blood pressure readings between a first example blood pressure monitor (BPM) 305 and a second example BPM 310 is shown. In general, the first BPM 305 and the second BPM 310 are each configured similar to the monitor 110 described above in connection with FIGS. 1-2.

However, in example embodiments, the first BPM 305 is an "office" device used by a healthcare professional (e.g., physician, medical assistant, etc.) to obtain "in-office" patient blood pressure readings, and optionally other vital information (e.g., temperature, pulse oximetry, etc.). In typical scenarios, the "office" device is a more robust device having more advanced functionality. With the advanced functionality, the "office" device is typically more expensive than other devices.

In contrast, the second BPM 310 is a "home" device used by a patient to obtain "at-home" blood pressure readings away from the office of the healthcare professional. Home monitoring is beneficial in many aspects. For example, home monitoring supplements blood pressure data obtained by the first BPM 305 to provide a healthcare professional with more information to better understand and manage patient blood pressure. Additionally, home monitoring enables identification of other blood pressure-related phenomena or comorbid conditions (e.g., white-coat hypertension, masked hypertension, etc.). In typical scenarios, the "home" device includes limited functionality in comparison to an "office device" and is generally designed to be easily used by the patient.

In some embodiments, the second BPM 310 is configured to obtain other patient vital information in addition to blood pressure readings, similar to the first BPM 305. However, despite similarities with respect to the type of diagnostic measurement capabilities of the first BPM 305 and the second BPM 310, these devices generally include different hardware components (e.g., different transducers, different signal conversion electronics, etc). Hardware differences between the first BPM 305 and second BPM 310 may lead to disparity between blood pressure readings obtained by each respective device over a similar time period.

For example, the first BPM 305 may calculate a systolic pressure "SYS1" 315 (see FIG. 3) of 126 mmHg and a diastolic pressure "DIA1" 320 of 80 mmHg from the raw oscillometric data of FIG. 2. In comparison, the second BPM 310 may calculate a systolic pressure "SYS2" 315 of 120 mmHg and a diastolic pressure "DIA2" 320 of 80 mmHg upon analysis of the same raw oscillometric data of FIG. 2. In this example, a difference of 6 mmHg is present between the two systolic pressure readings.

To address this issue, the first BPM 305 and the second BPM 310 are compatibly configured to enable correlation between obtained blood pressure readings. For example, in one embodiment, a blood pressure cuff 335 of the second BPM 310 is secured to the patient 105, and a connector 340 of a tubing assembly 345 of the first BPM 305, comprising the connector 340 and a tube 350, is coupled to a pneumatic pass-through port 355 of the second BPM 310. The pneumatic pass-through port 355 is an external connector that is in fluid connection with internal components (e.g., pressure transducer) and the blood pressure cuff 335 of the second BPM 310. In this manner, the first BPM 305 and the second BPM 310 are mechanically connected in series to form a continuous, sealed fluid connection between the first BPM 305 and the blood pressure cuff 335.

Following mechanical connection of the first BPM 305 to the second BPM 310, the first BPM 305 is used to drive the blood pressure cuff 335 as part of an oscillometric blood pressure measurement for the purpose of deriving and/or calculating a pressure offset correction parameter. More specifically, the first BPM 305 and the second BPM 310 are approximately simultaneously exposed to the same oscillometric data (e.g., envelope 215) during the measurement, by virtue of being connected in series. Any difference between the final blood pressure readings calculated by the first BPM 305 and the second BPM 310 (e.g., 6 mmHg) is recorded as the correction parameter. The correction parameter is then used to adjust future blood pressure readings of the second BPM 310 such that these readings can be validly compared (i.e., "apples-to-apples") with those calculated by the first BPM 305.

In general, the pressure offset as quantified by the correction parameter is attributed at least partially to differences in hardware between the first BPM 305 and the second BPM 310, as the statistical algorithm used to calculate blood pressure is common to these two devices. Additionally, the correction parameter may be stored within either one or both of the first BPM 305 and the second BPM 310 and/or in another pre-defined location (e.g., HIPAA compliant medical record, database, etc.) for future use in presenting blood pressure trend data.

Figure 4:
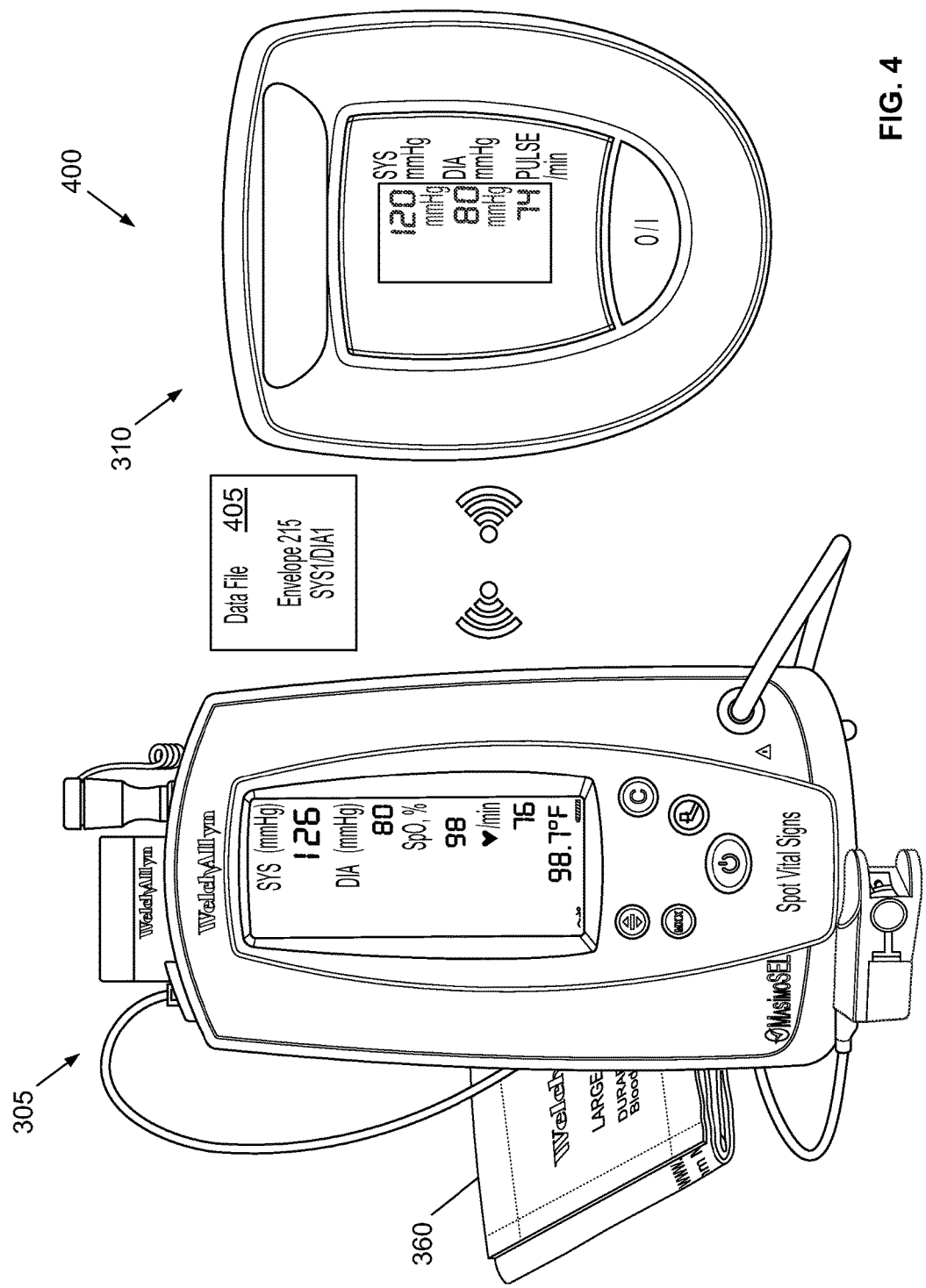
FIG. 4 shows a second example system for correlating blood pressure readings between first and second blood pressure monitors.
Figure 6:
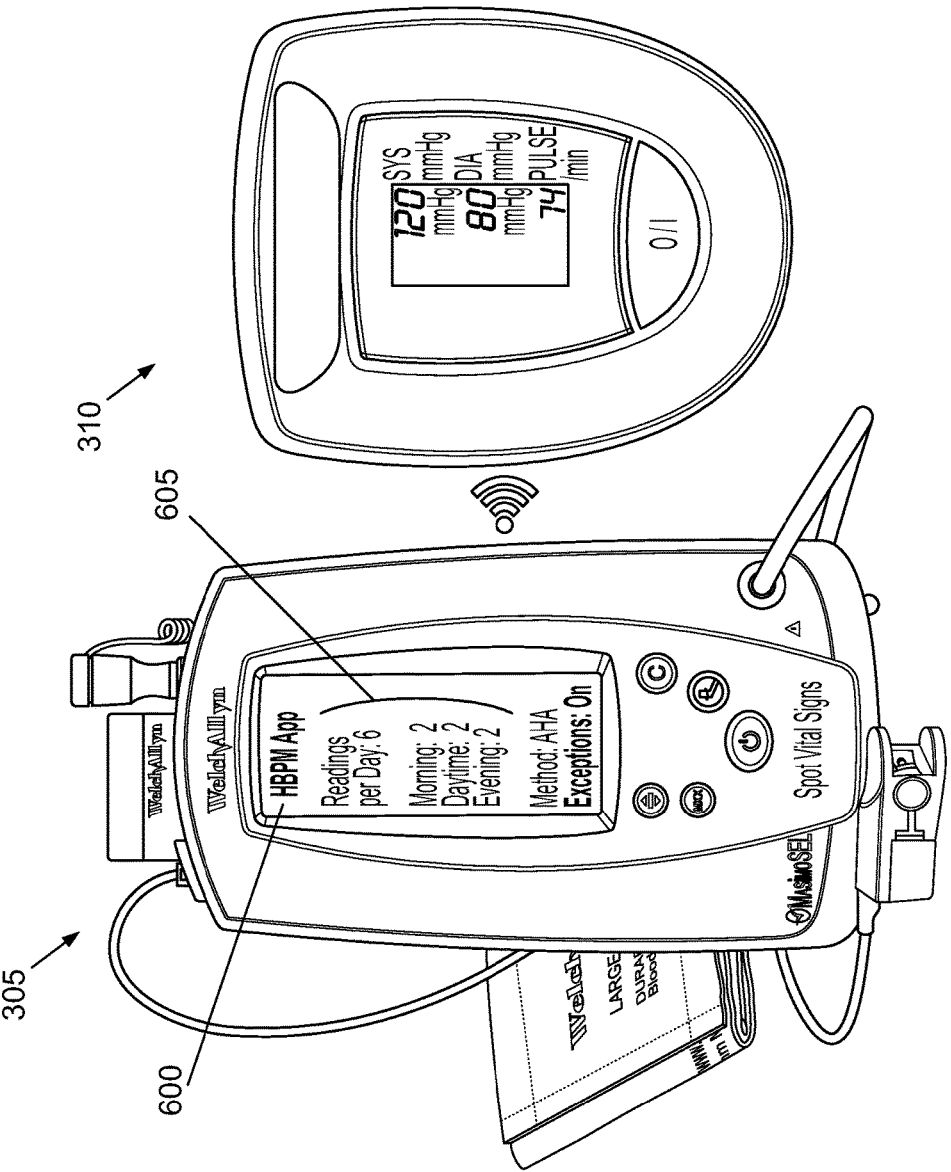
FIG. 6 shows a software application of an office blood pressure monitor used to define a blood pressure reading schedule.

Referring now to FIG. 4, a second example system 400 for correlating blood pressure readings between the first BPM 305 and the second BPM 310 of FIG. 3 is shown. In this example, a blood pressure cuff 360 of the first BPM 305 is secured to the patient 105, and then the first BPM 305 is used to perform an oscillometric blood pressure measurement to calculate patient systolic and diastolic pressure values (e.g., SYS1/DIA1=126/80). The raw oscillometric data (e.g., envelope 215) used by the first BPM 305 to calculate these pressure values is saved within a data file 405 by the first BPM 305, along with the systolic and diastolic pressure values calculated by the first BPM 305.

In addition to the pressure values, in some embodiments the data file 405 can include configuration data. For example, the data file 405 can include configuration data relating to how the first BPM 305 is configured, such as the settings used to obtain the pressure values. Examples of such configuration data include set-up and pneumatic information, such as pressure presets, etc. In this example, the configuration data that is sent by the first BPM 305 can be used to configure the second BPM 310.

Following population of the data file 405 by the first BPM 305, the data file 405 is subsequently transmitted to the second BPM 310 via wireless communication (e.g., Bluetooth, ZigBee, etc.). The second BPM 310 is configured to receive and process the data file 405 to calculate values of the systolic and diastolic pressures (e.g., SYS2/DIA2=120/80) from the same raw oscillometric data used by the first BPM 305.

Any difference between the final blood pressure readings calculated by the first BPM 305 and the second BPM 310 (e.g., (SYS1–SYS2)=6 mmHg) is recorded as the pressure offset correction parameter. Similar to the workflow described above on connection with FIG. 3, the correction parameter may then be stored within either one or both of the first BPM 305 and the second BPM 310 and/or in another pre-defined location for future use in presenting blood pressure trend data.

The example workflows described above in connection with FIGS. 3 and 4 for correlating blood pressure readings between an office BPM and a home BPM are beneficial in many respects. For example, in many instances a healthcare professional may express a general distrust of blood pressure readings generated by a home BPM, as these readings typically do not correlate well or directly with blood pressure readings generated by an office BPM. However, when the blood pressure readings of the first BPM 305 and the second BPM 310 are shown to correlate, a more complete and reliable blood pressure trend may be developed and used for managing one or more patient medical conditions.

Figure 5:
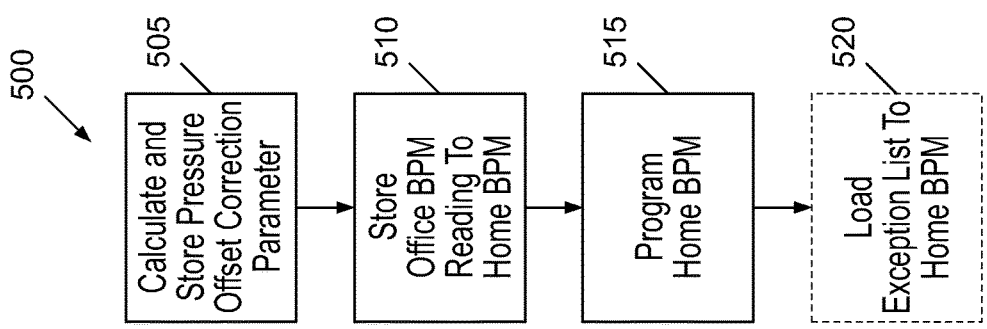
FIG. 5 shows an example method for configuring a home blood pressure monitor for initial use by a patient.

Referring now to FIG. 5, an example method 500 for configuring the second BPM 310 of FIG. 3 for use by the patient 105 of FIG. 1 is shown. In general, the second BPM 310 is configured by a healthcare professional using the first BPM 305 while the patient is "in-office." Other embodiments are possible as well.

The method 500 begins at an operation 505. At operation 505, a pressure offset correction parameter is calculated and stored for the purpose of correlating blood pressure readings between the first BPM 305 and the second BPM 310. In one embodiment, the correction parameter is calculated and stored in accordance with the workflow described above in connection with FIG. 3. In another embodiment, the correction parameter is calculated and stored in accordance with the workflow described above in connection with FIG. 4. Still other embodiments are possible.

Next, at an operation 510, an "in-office" blood pressure reading calculated by the first BPM 305 (e.g., SYS1/DIA1=126/80) as part of an oscillometric blood pressure measurement is stored within the second BPM 310. The "in-office" blood pressure reading may generally be wirelessly transferred to the second BPM 310 for storage or optionally extracted from the data file 405 by the second BPM 310 for storage, based on the method and/or workflow used to calculate the correction parameter at operation 505. As described in detail below in connection with FIGS. 7-9, the "in-office" blood pressure reading is used to "trigger" exceptions and/or "flag" future blood pressure readings obtained by the second BPM 310.

Next, at an operation 515, a software application executing on the first BPM 305 is used to program the second BPM 310 for use by the patient 105. For example, referring now additionally to FIG. 6, an application 600 of the first BPM 305 is used to confirm and/or adjust a configurable and patient-specific blood pressure reading schedule 605. In the example shown, the schedule 605 corresponds to the American Heart Association preferred blood pressure reading schedule of six (6) "Readings per Day" in which two (2) respective readings are scheduled to be performed each during "Morning" and "Daytime" and "Evening." Other embodiments are possible.

The schedule 605 is then transmitted (e.g., via wireless and/or hardwire connection) to the second BPM 310, which is configured to receive and process the schedule 605. In some embodiments, date/time settings of the second BPM 310 are additionally synchronized to the date/time settings of the first BPM 305 during or following transfer of the schedule 605 between the two devices.

Referring again to FIG. 5, an exception list is optionally transmitted to the second BPM 310 at an operation 520. An example exception list is described below in connection with FIGS. 7-9. The second BPM 310 is configured to receive and internally process the exception list, which is in turn displayed by the second BPM 310 when a blood pressure reading obtained by the second BPM 310 differs "significantly" in magnitude from the "in-office" reading stored within the second BPM 310 at operation 510, also described further below.

Figure 7:
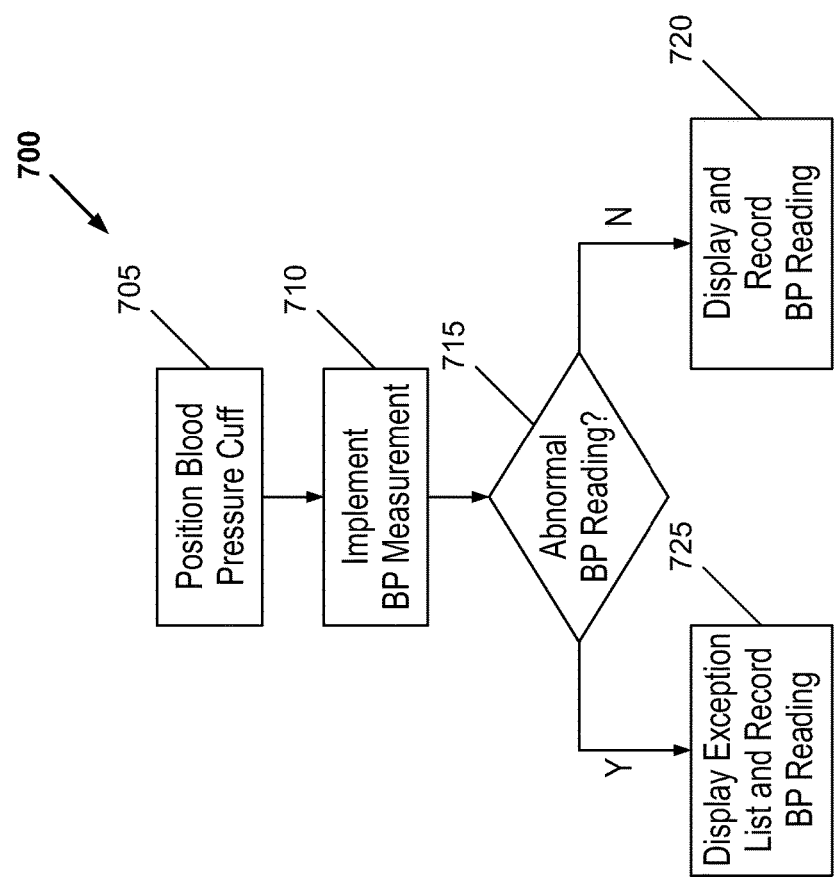
FIG. 7 shows an example method for using a home blood pressure monitor.

Referring now to FIG. 7, an example method 700 for using the second BPM 310 is shown in accordance with the present disclosure. In the example embodiment, the second BPM 310 is used by the patient 105 to supplement "in-office" blood pressure data obtained by the first BPM 305 to provide a healthcare professional with more information to understand and manage patient blood pressure. Additionally, use of the second BPM 310 to obtain "at-home" blood pressure readings enables identification of other blood pressure-related phenomena or comorbid conditions.

The method 700 begins at an operation 705. At operation 705, the blood pressure cuff 335 of the second BPM 310 is positioned to the patient 105 for the purpose of obtaining an oscillometric blood pressure measurement.

Next, at an operation 710, the patient 105 initiates the measurement upon selection of a corresponding control mechanism (e.g., start button) of the second BPM 310. In the example embodiment, the second BPM 310 calculates values of the systolic and diastolic pressures (e.g., SYS2/DIA2=120/80) upon analysis of raw oscillometric data (e.g., envelope 215) that is obtained in a manner similar to that described above in connection with FIGS. 1-6.

Figure 8:
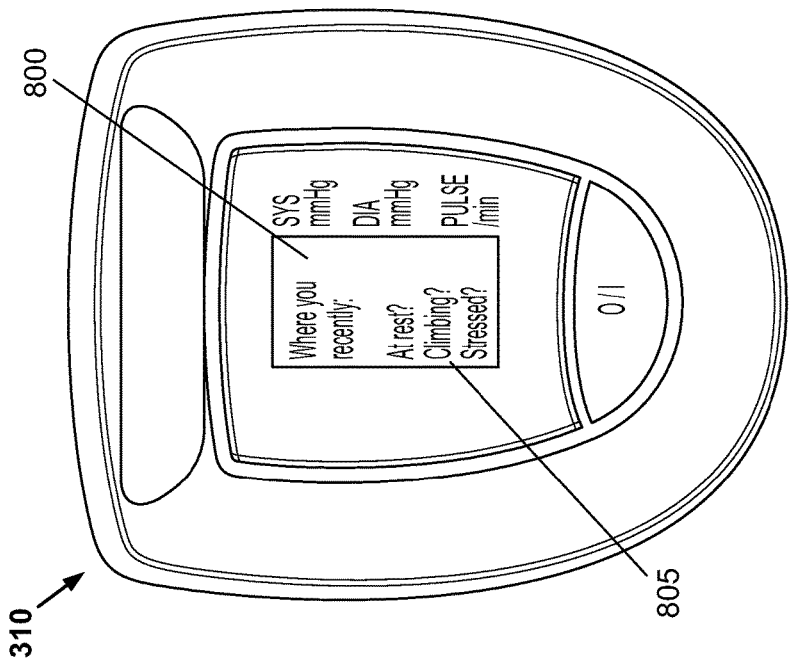
FIG. 8 shows an example exception list that is displayed by a home blood pressure monitor.

Next, at operation 715, the second BPM 310 compares the "at-home" blood pressure reading calculated at operation 710 to a stored "in-office" blood pressure reading to determine whether the "at-home" reading is potentially "abnormal." For example, referring now additionally to FIG. 8, an exception list 800 is displayed by the second BPM 310 when the blood pressure reading calculated at operation 710 sufficiently differs in magnitude from the stored "in-office" reading based on a pre-defined rule (e.g., |SYS1−SYS2|>5 mmHg; |SYS1−SYS2|>3 mmHg AND |DIA1−DIA2|>4 mmHg, |SYS1−SYS2|>4 mmHg OR |DIA1−DIA2|>2 mmHg etc.). When the condition(s) of the pre-defined rule is satisfied, one or more items 805 are displayed (e.g., "Stressed?") for optional selection by the patient 105 for the purpose of providing context to the "abnormal" blood pressure reading. Other embodiments are possible.

For example, in some embodiments, the "at-home" blood pressure reading is further compared to the "in-office" blood pressure reading stored within the second BPM 310 for the purpose of identifying white-coat hypertension, a phenomenon in which patients exhibit elevated blood pressure in a clinical setting but not in other settings. For example, when the "at-home" blood pressure reading is "significantly" less than the "in-office" blood pressure reading (e.g., (SYS1−SYS2)≥5 mmHg), the second BPM 310 flags or documents the "at home" blood pressure reading. Such an arrangement beneficially enables a physician to obtain a more accurate picture of patient blood pressure readings and/or trends. Other embodiments are possible.

When the "at-home" blood pressure reading calculated at operation 710 is evaluated as "normal" at operation 715, process flow proceeds to an operation 720 in which the blood pressure reading is both displayed (e.g., SYS2/DIA2=120/80) and stored to the second BPM 310 for future use, as described in further detail below in connection with FIGS. 10-11. When the "at-home" blood pressure reading is evaluated as "abnormal" at operation 715, process flow proceeds to an operation 725 in which both the exception list 800 of FIG. 8 is displayed and the blood pressure reading is stored to the second BPM 310 for future use.

Figure 9:
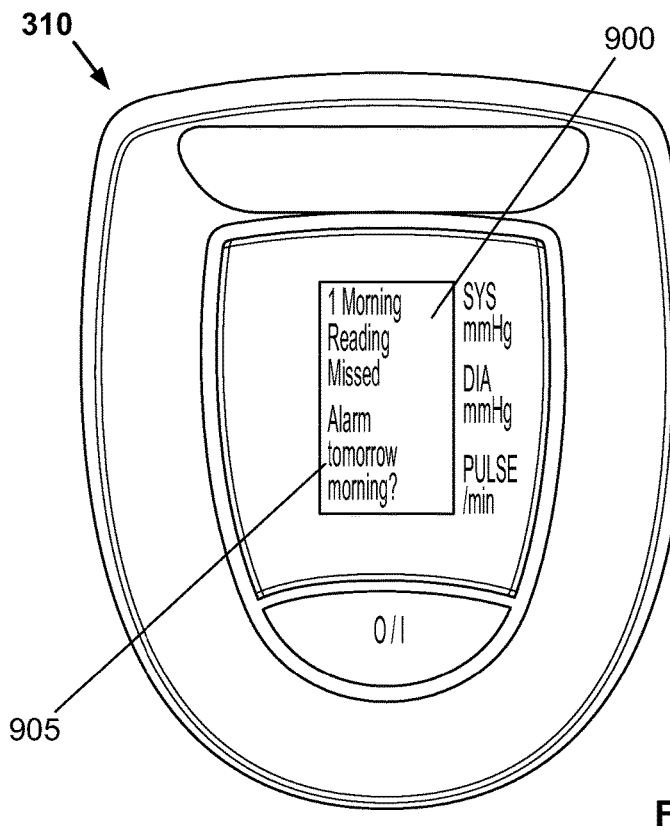
FIG. 9 shows an example notification indicating one or more missed blood pressure readings.

In general, the second BPM 310 is configured to help the patient properly use the second BPM 310. In some embodiments, a notification is shown on a display of the second BPM 310 indicating one or more "missed" blood pressure readings. For example, FIG. 9 shows an example notification 900 indicating "1 Morning Reading Missed" and also shows a text 905 "Alarm tomorrow morning?" that is optionally selectable by the patient 105 to program the second BPM 310 to alert the patient 105 such that another "morning" blood pressure reading is not missed. In this manner, the example notification 900 increases patient compliance.

Figure 10:
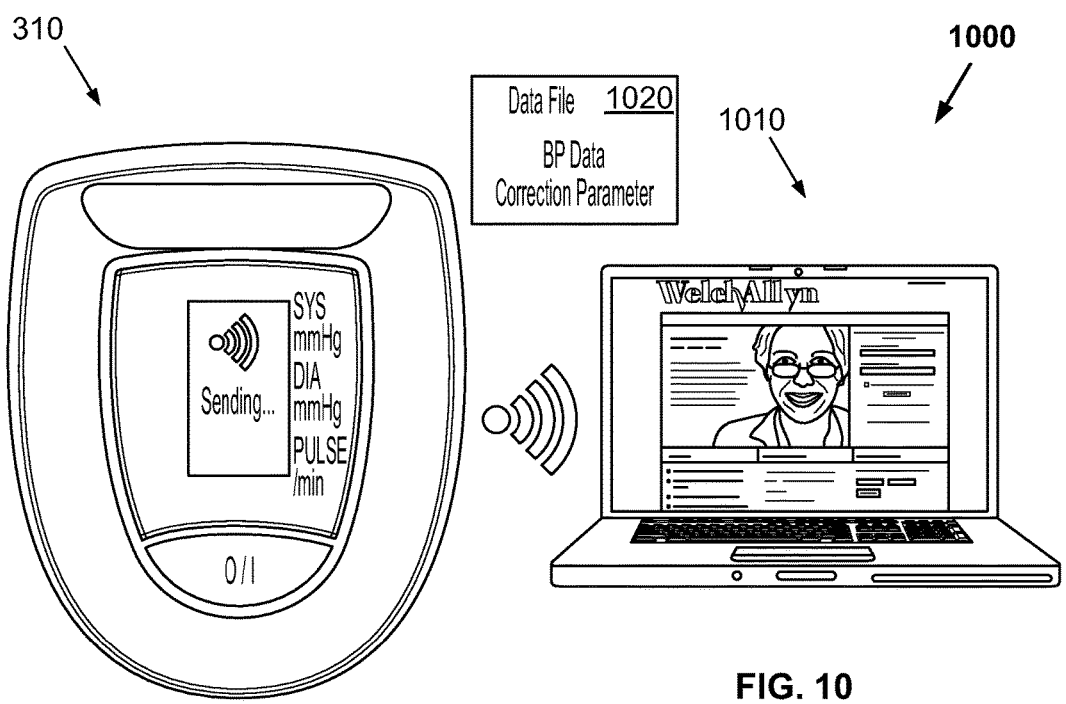
FIG. 10 shows an example environment for uploading and viewing blood pressure data obtained by a home blood pressure monitor to a web portal.
Figure 11:
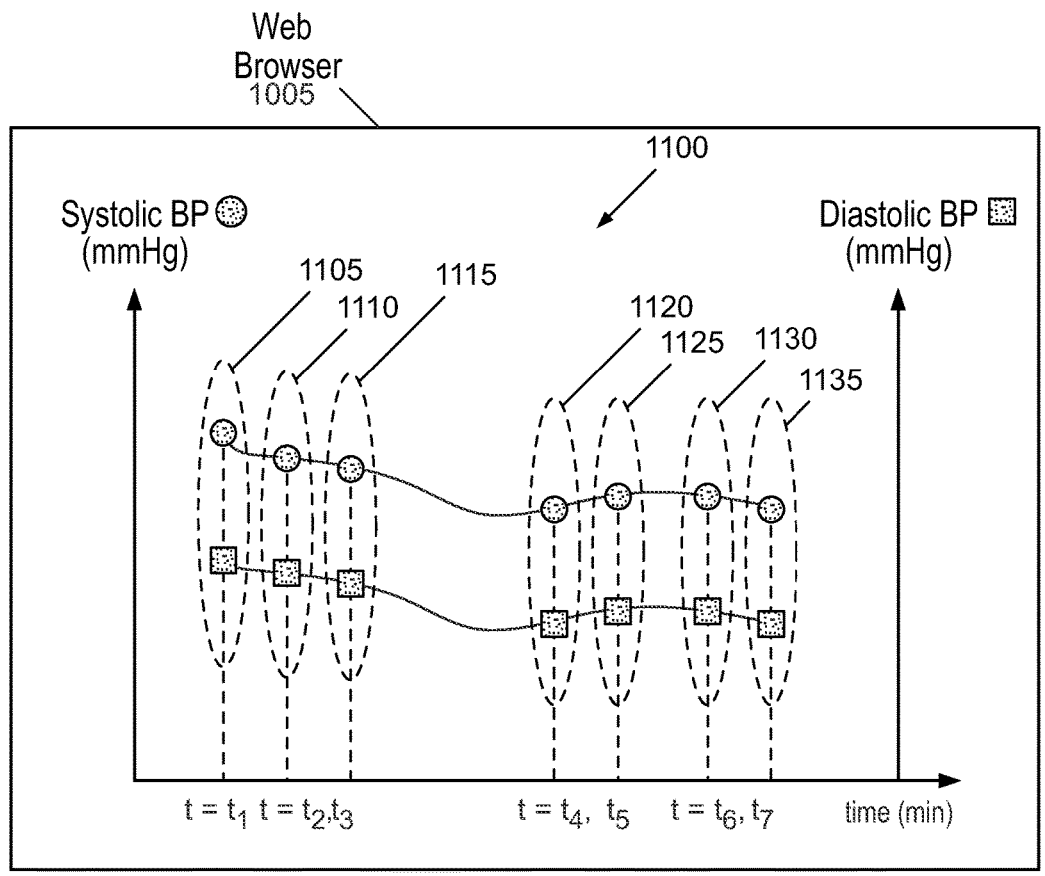
FIG. 11 shows an example pressure curve illustrating blood pressure trend data of a patient.

Referring now to FIG. 10, an example computing environment 1000 configured for uploading and viewing blood pressure data obtained by the second BPM 310 is shown. In this example, either the patient 105 or a healthcare professional initially accesses a web portal via a web browser 1005 executing on a computing device 1010. A communication link is then automatically or manually established to communicatively connect the second BPM 310 to the computing device 1010. Following establishment of the communication link, a data file 1020 including all time-stamped blood pressure data obtained by the second BPM 310 and a pressure offset correction parameter is transferred to the computing device 1010. The correction parameter being previously calculated and stored within the second BPM 310 in a manner similar to that described above in connection with FIGS. 1-9.

The example computing device 1010 is configured to receive and transfer all information within the data file 1020 to the web portal via a network connection (not shown). Subsequently, the patient 105 or a healthcare professional can access the web portal via the web browser 1005 to view blood pressure trend data over a configurable time period. For example, referring now to additionally to FIG. 11, an example pressure curve 1100 is shown illustrating blood pressure trend data of the patient 105 over an example time period t=24 hours.

In the example shown, a first data point 1105 taken at time t=$t_1$ in late afternoon corresponds to an initial "in-office" blood pressure reading obtained by the first BPM 305. In contrast, a second data point 1110 taken at time t=$t_2$ and a third data point 1115 taken at time t=$t_3$ each correspond to an "at-home" blood pressure reading obtained by the second BPM 310 in accordance with a predefined schedule (e.g., schedule 605). The second data point 1110 and third data point 1115 being both taken by the patient 105 in the evening of the same day that the first data point 1105 was taken.

Similarly, a fourth data point 1120 taken at time t=$t_4$ and a fifth data point 1125 taken at time t=$t_5$ corresponds to "at-home" blood pressure readings obtained by the second BPM 310, both taken in the morning following the day that the first data point 1105 was taken. Lastly, a sixth data point 1130 taken at time t=$t_6$ and a seventh data point 1135 taken at time t=$t_7$ corresponds to "at-home" blood pressure readings obtained by the second BPM 310, both taken in the afternoon following the day that the first data point 1105 was taken.

In example embodiments, the data points 1110-1135 as obtained by the second BPM 310 are plotted on the pressure curve 1100 taking into account the pressure offset correction parameter as defined within the data file 1020. In this manner, the blood pressure readings associated with these data points are correlated and consistent with the blood pressure reading of the first data point 1105 calculated by the first BPM 305. Other embodiments are possible.

Figure 12:
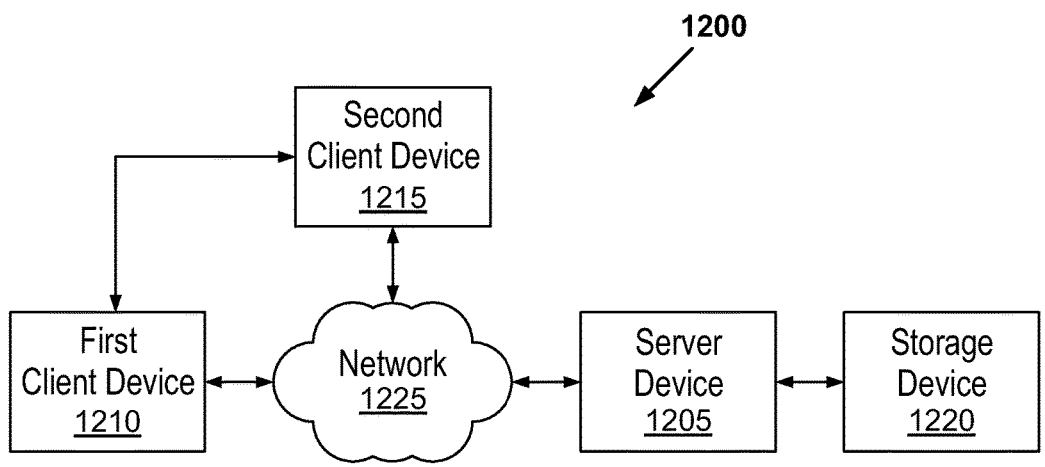
FIG. 12 shows an example networked computing environment.

Referring now to FIG. 12, an example networked environment 1200 is shown in accordance with the present disclosure. The networked environment 1200 includes a server device 1205, a first client device 1210, a second client device 1215, a storage device 1220, and a network 1225. Other embodiments are possible. For example, the networked environment 1200 may generally include more or fewer devices, networks, and other components as desired.

The server device 1205, first client device 1210, and second client device 1215 are computing devices, described in further detail below in connection with FIG. 13.

The storage device 1220 is an electronic data storage device, such as a relational database or any other type of persistent data storage device. The storage device 1220 stores data in a predefined format such that the server device 1205 can query, modify, and/or manage electronic data stored thereon. Example electronic data includes information related to HIPAA protected patient-specific medical information (e.g., blood pressure data, medical history, etc.). Other embodiments of the storage device 1220 are possible.

The network 1225 is a bi-directional data communication path for data transfer between one or more devices. In the example shown, the network 1225 establishes a communication path for data transfer between the server device 1205, first client device 1210, and the second client device 1215. However, in the example shown, the first client device 1210 and the second client device 1215 are additionally configured to communication directly (e.g., via wireless and/or hardwire connection).

In general, the network 1225 can be of any of a number of wireless or hardwired WAN, LAN, Internet, or other packet-based communication networks such that data can be transferred among the respective elements of the networked environment 1200. Other embodiments of the network 1225 are possible.

Figure 13:
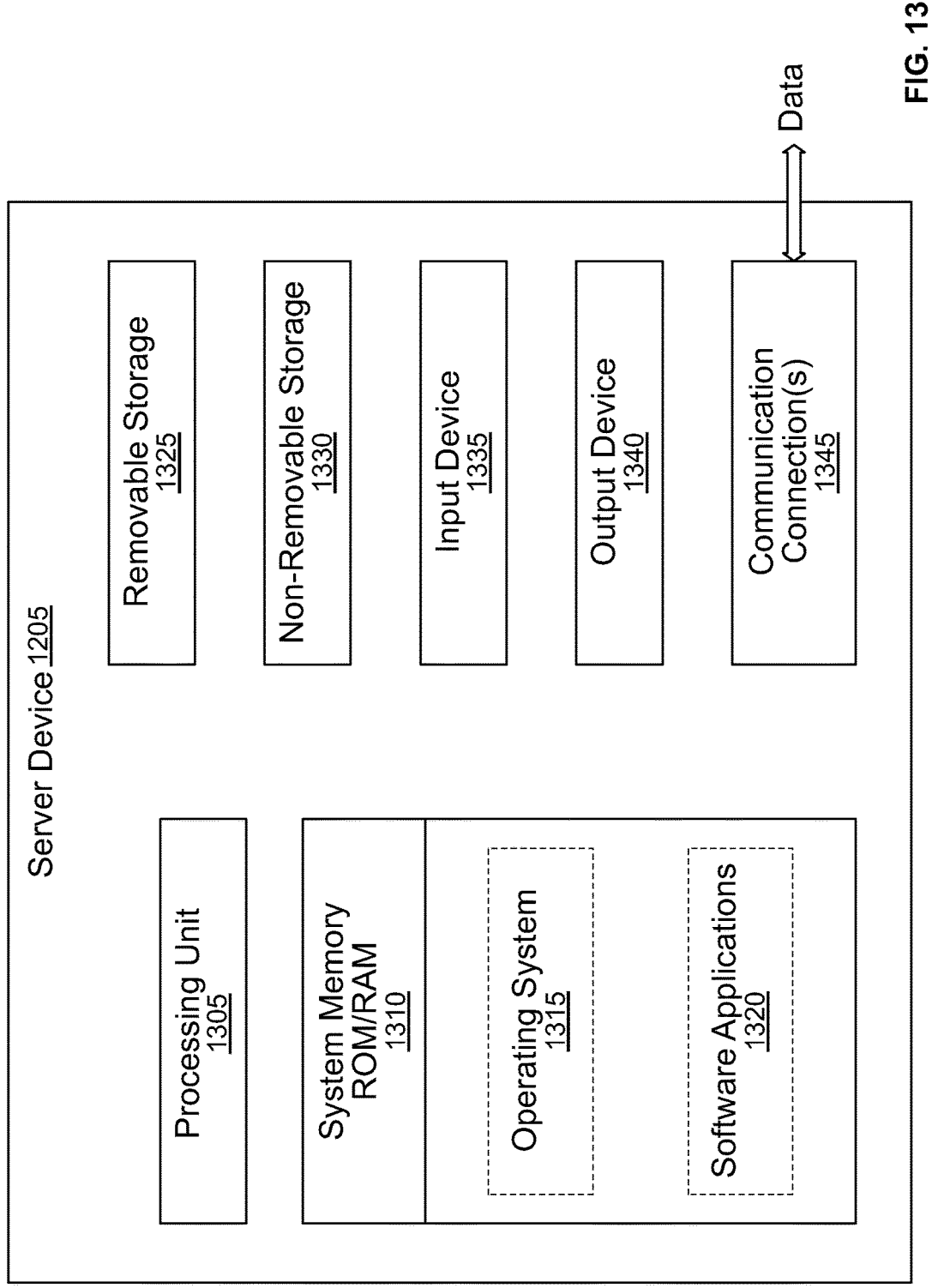
FIG. 13 shows a server computing device of the networked computing environment of FIG. 12.

Referring now to FIG. 13, the server device 1205 of FIG. 12 is shown in further detail. As mentioned above, the server device 1205 is a computing device. An example computing device includes a desktop computer, laptop computer, server computer, personal data assistant, smartphone, netbook, notebook, and many others.

The server device 1205 includes a processing unit 1305 and a system memory 1310. The system memory 1310 stores an operating system 1315 for controlling the operation of the server device 1205 and/or another computing device(s). The system memory 1310 further includes one or more software applications 1320. Software applications 1320 include many different types of single and multiple-functionality programs, such as a server program, a web browser program, an electronic mail program, and many others. An example server program is portal server that hosts and/or provides access to functionality associated with a web portal. Other embodiments are possible.

The system memory 1310 is computer-readable media. Examples of computer-readable media include computer storage media and communication media. Computer storage media is physical and/or tangible media that is distinguished from communication media.

Computer storage media includes physical volatile and non-volatile, removable and non-removable media implemented in any method or technology for storage of information such as computer-readable instructions, data structures, program modules, or other data. Computer storage media also includes, but is not limited to, RAM, ROM, EEPROM, flash memory or other memory technology, CD-ROM, DVD or other optical storage, magnetic cassettes, magnetic tape, magnetic disk storage or other magnetic storage devices, or any other physical medium which can be used to store the desired information and which can be accessed by the server device 1205. Any such computer storage media may be part of or external to the server device 1205. Such storage is illustrated in FIG. 13 by removable storage 1325 and non-removable storage 1330.

Communication media is typically embodied by computer-readable instructions, data structures, program modules, or other data, in a modulated data signal, such as a carrier wave or other transport mechanism, and includes any information delivery media. The term "modulated data signal" describes a signal that has one or more of its characteristics set or changed in such a manner as to encode information in the signal. By way of example, communication media includes wired media such as a wired network or direct-wired connection, and wireless media such as acoustic, RF, infrared and other wireless media.

The server device 1205 also includes any number and type of an input device 1335 and output device 1340. An example input device 1335 includes a keyboard, mouse, pen, voice input device, touch input device, and others. An example output device 1340 includes a display, speakers, printer, and others. The server device 1205 also includes a communication connection 1345 configured to enable communications with other computing devices directly and/or over a network (e.g., network 1225) in a distributed computing system environment.

The first client device 1210 and the second client device 1215 are generally configured similar to the server device 1205 as described in connection with FIG. 12. In example embodiments, the first client device 1210 is additionally configured as a programmable automated blood pressure machine (e.g., monitor 110, first BPM 305, second BPM 310, etc.) to perform an oscillometric blood pressure measurement. The second client device 1215 is a special purpose computing device (e.g., computing device 1010) configured to enable a user to access and/or implement functionality of the server device 1205 and the first client device 1210. Other embodiments are possible.

The example embodiments described herein can be implemented as logical operations in a computing device in a networked computing system environment. The logical operations can be implemented as: (i) a sequence of computer implemented instructions, steps, or program modules running on a computing device; and (ii) interconnected logic or hardware modules running within a computing device.

For example, the logical operations can be implemented as algorithms in software, firmware, analog/digital circuitry, and/or any combination thereof, without deviating from the scope of the present disclosure. The software, firmware, or similar sequence of computer instructions can be encoded and stored upon a computer readable storage medium and can also be encoded within a carrier-wave signal for transmission between computing devices.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for correlating diagnostic measurements obtained by at least two different medical devices, the method comprising:

obtaining a first diagnostic measurement at a location on a patient by initiating a first oscillometric blood pressure measurement reading with a first medical device using a first inflatable cuff inflated to a pressure exceeding a systolic arterial pressure;

obtaining configuration data of the first medical device, the configuration data including set-up information and pneumatic information;

configuring a second medical device based on the configuration data of the first medical device;

obtaining a second diagnostic measurement at the same location on the patient by initiating a second oscillometric blood pressure measurement reading with the second medical device using the first inflatable cuff or a second inflatable cuff inflated to the pressure exceeding the systolic arterial pressure;

generating, by a processing unit, a correction parameter by comparing the first and second diagnostic measurements, wherein the correction parameter includes a pressure offset correction parameter that quantifies a difference in oscillometric blood pressure measured by the first medical device and the second medical device;

storing the correction parameter in the second medical device;

obtaining, by the second medical device, a blood pressure measurement; and adjusting the blood pressure measurement using the correction parameter by offsetting the blood pressure measurement by the pressure offset correction parameter.

2. The method of claim 1, wherein the first diagnostic measurement is a first blood pressure value and the second diagnostic measurement is a second blood pressure value.

3. The method of claim 2, further comprising mechanically coupling the first medical device and the second medical device.

4. The method of claim 3, further comprising approximately simultaneously calculating, by the processing unit, the first and second blood pressure values.

5. The method of claim 4, further comprising calculating, by the processing unit, the first and second blood pressure values from the first and second oscillometric blood pressure measurement readings.

6. The method of claim 2, further comprising calculating, by the processing unit, the first blood pressure value from the first oscillometric blood pressure measurement reading.

7. The method of claim 6, further comprising wirelessly transmitting the first blood pressure value and the first oscillometric blood pressure measurement reading to the second medical device.

8. The method of claim 7, further comprising calculating, by the processing unit, the second blood pressure value from the second oscillometric blood pressure measurement reading.

9. The method of claim 2, further comprising transferring, by the processing unit, at least the first blood pressure value and the second blood pressure value to a web portal from the second medical device.

10. The method of claim 9, further comprising generating, by the processing unit, a blood pressure trend plot including at least the first blood pressure value and the second blood pressure value.

* * * * *